(12) United States Patent
Klewer et al.

(10) Patent No.: US 8,716,629 B2
(45) Date of Patent: May 6, 2014

(54) TEMPERATURE SENSOR FOR BODY TEMPERATURE MEASUREMENT

(75) Inventors: Jasper Klewer, Eindhoven (NL); Amy Cheung, Eindhoven (NL); Liesbeth Van Pieterson, Eindhoven (NL); Erik Bakkers, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 56 days.

(21) Appl. No.: 13/262,241

(22) PCT Filed: Apr. 1, 2010

(86) PCT No.: PCT/IB2010/051418
§ 371 (c)(1),
(2), (4) Date: Sep. 30, 2011

(87) PCT Pub. No.: WO2010/116297
PCT Pub. Date: Oct. 14, 2010

(65) Prior Publication Data
US 2012/0024833 A1  Feb. 2, 2012

(30) Foreign Application Priority Data
Apr. 6, 2009  (EP) .................................... 09157392

(51) Int. Cl.
*H05B 1/00* (2006.01)
*G01K 1/08* (2006.01)
(52) U.S. Cl.
USPC .......................................... 219/211; 374/141
(58) Field of Classification Search
USPC ................. 219/209, 202, 211, 217, 494, 529; 374/151
See application file for complete search history.

(56) References Cited

U.S. PATENT DOCUMENTS 3,933,045 A * 1/1976 Fox et al. ........................ 374/134
4,686,998 A * 8/1987 Robbins ......................... 600/483
(Continued)

FOREIGN PATENT DOCUMENTS

CN  1247628 A  3/2000
WO  9816938 A1  4/1998

OTHER PUBLICATIONS

Dittmar, A., et al.; A Non Invasive Wearable Sensor for the Measurement of Brain Temperature; 2006; IEEE Trans. on Intl. Conf. of the Engineering in Medicine and Biology Society; pp. 900-902.

(Continued)

*Primary Examiner* — Lisa Caputo
*Assistant Examiner* — Nasir U Ahmed

(57) ABSTRACT

This invention relates to a temperature sensor for body temperature measurements. The temperature sensor is made of several layers, where a first layer has a central heater embedded therein, a second layer which is attached to the first layer has at least one first thermistor embedded therein for measuring a first temperature value, a third layer has at one ore second thermistor embedded therein separated from the first thermistor for measuring at least one second temperature value, but this third layer is adapted to be in contact to the skin of the surface of the body for conducting the heat escaping from the body through the layers. The difference between the first and the second temperature values indicates the heat flux from the body. The heat emitted from central heater is tuned oppositely to the heat flux until a zero heat flux is reached, where the temperature at the at least one second thermistor at zero heat flux indicates the body temperature. These layers are fabric layers.

19 Claims, 2 Drawing Sheets

(56) References Cited

U.S. PATENT DOCUMENTS

| | | | | |
|---|---|---|---|---|
| 6,888,112 | B2* | 5/2005 | Rock et al. | 219/545 |
| 6,890,096 | B2* | 5/2005 | Tokita et al. | 374/163 |
| 7,202,443 | B2* | 4/2007 | Rock et al. | 219/211 |
| 7,284,904 | B2* | 10/2007 | Tokita et al. | 374/164 |
| 7,329,389 | B2* | 2/2008 | Horovitz et al. | 422/83 |
| 7,365,661 | B2* | 4/2008 | Thomas | 341/117 |
| 7,394,395 | B2* | 7/2008 | Sakatani et al. | 340/679 |
| 2006/0060576 | A1* | 3/2006 | Haas et al. | 219/543 |
| 2007/0239992 | A1* | 10/2007 | White et al. | 713/186 |
| 2008/0083740 | A1* | 4/2008 | Kaiserman et al. | 219/520 |

OTHER PUBLICATIONS

Lymberis, A., et al.; Advanced Wearable Health Systems and Applications; 2007; IEEE Engineering in Medicine and Biology; pp. 29-33.

Noury, N., et al.; A Smart Cloth for Ambulatory Telemonitoring of Physiological Parameters and Activity: The VTAMN Project; 2004; Proc. Intl. Workshop on Enterprise Networking and Computing in Healthcare Industry; pp. 155-160.

Yamakage, M., et al.; Deep temperature monitoring using a zero-heat-flow method; 2003; Journal of Anesthesia; 17 (2)108-115.

* cited by examiner

TEMPERATURE SENSOR FOR BODY TEMPERATURE MEASUREMENT

FIELD OF THE INVENTION

The present invention is related to a temperature sensor for body temperature measurements, and to a garment comprising the temperature sensor.

BACKGROUND OF THE INVENTION

In the recent years, there has been some development in developing core body temperature sensors. A heat flux temperature sensor is an example of such a core body temperature sensor, but the measuring is based on so-called zero heat flux principle, but this principle is used in the "low power core body temperature monitoring" for continuous temperature monitoring of patients. According to this principle the core body temperature is measured by placing the sensor on the skin of e.g. the forehead of the patient. An accurate temperature measurement requires that the sensor is flexible so that it follows that skin surface so as to ensure that there are no air gaps between the skin and sensor, which otherwise can have adverse effect on the measurement accuracy.

Although the prior art heat flux temperature sensors are somewhat flexible, they are suitable for high acuity applications, e.g. during surgery where the sensor monitors the core body temperature during the surgery and where the patient is not moving.

However, for applications where the skin is actually moving more, e.g. for monitoring temperature of newborns, or more general use (e.g. outside the hospital) their use is somewhat limited due to the lack of flexibility needed to follow the skin surface. Also the prior art sensors are obtrusive, either for newborns requiring an adhesive on the skin, or for non-high acuity applications being visible on the patient's forehead, changing the appearance of the patient.

SUMMARY DESCRIPTION OF THE INVENTION

The object of the present invention is to overcome the above mentioned drawbacks by providing a temperature sensor with enhanced flexibility.

According to a first aspect the present invention relates to a temperature sensor for body temperature measurements, comprising:
- a first layer having a central heater embedded therein,
- a second layer attached to the first layer having at least one first thermistor embedded therein for measuring a first temperature value,
- at least one third layer having at least one second thermistor embedded therein separated from the first thermistor for measuring at least one second temperature value, the at least one third layer being adapted to be in contact to the skin of the surface of the body for conducting the heat escaping from the body through the layers, the difference between the first and the second temperature values indicating the vertical heat flux from the body, where the heat emitted from central heater is tuned oppositely to the vertical heat flux until a zero heat flux is reached, where the temperature at the at least one second thermistor at zero heat flux indicates the body temperature, wherein the first, second and at least the third layer are fabric layers.

Accordingly, a very flexible temperature sensor is provided which follows the skin of the body and that can easily be integrated into garment, such as a cap, baby cap, headband, shirt, diaper and belt, and even into a bed object such as a pillow, blanket or seat which is in contact with the body. Another advantage offered by the flexible body temperature is comfort, while not critical in the high acuity setting, is of great importance in the low acuity setting and use outside of the hospital.

In one embodiment, the layers are stitched or laminated together, interwoven, or combination thereof.

In one embodiment, the first and the second layers are made of the same fabric and form a single functional layer having the central heater and the at least one first thermistor embedded therein such that they are separated from each other.

In one embodiment, the central heater is stitched, or embroidered, or woven, or laminated into the first layer using conductive yarn. The conductive yarn can for example be a metal coated polymer such as Ag-coated polyester, stainless steel (containing) yarn or Cu wire (with or without silver coating).

In one embodiment, the dimension of the central heater is adapted to the depth of measurement such that the larger the depth is to be measured the larger becomes the dimension of the central heater.

In one embodiment, the central heater is printed onto the first layer using conductive ink or conductive paste.

In one embodiment, the central heater is made of a conductive material with a resistance between 5-150 ohm/meter.

In one embodiment, the thermistors are attached to a woven, stitched or knitted conductive circuit.

In one embodiment, the conductive circuit is made of conductive material having a resistance lower 20 ohm/meter.

In one embodiment, the fabric layers are made of woven or non-woven fabrics.

In one embodiment, the second and the at least the third layers are separated by a flexible heat insulating layer. The flexible heat insulating layer may as an example be selected from: neoprene (polychloroprene), PVDF, EPDM (ethylene propylene diene monomer), and foam type materials polyethylene (PE), polypropylene (PP), methylacrylate (EMA), ethylenevinylacetate (EVA), polyolefin.

In one embodiment, the temperature sensor further comprises an insulating layer applied on top of the first layer. In that way, heat losses may be prevent and thus a less power is required to run the sensor.

In one embodiment, the temperature sensor further comprises a transmitter for transmitting the temperature measured at the at least one second thermistor at zero heat flux to an external monitoring device comprising a receiver. Accordingly, the temperature can be continuously monitored via e.g. a wireless communication link. This is of particular advantage when monitoring e.g. newborns where the measured temperature is displayed on the external monitoring device (e.g. babyphone).

In one embodiment, the temperature sensor is integrated into patch.

In one embodiment, the patch further comprises a processing unit for converting the output from the at least one second thermistor at zero heat flux into the measured body temperature, a battery, and an indicator means for indicating the measured body temperature. This patch can be made so that it is either re-usable or disposable. Accordingly, this allows unobtrusive temperature monitoring, e.g. for children with fewer.

In one embodiment, the temperature sensor further comprises a side thermistor arranged at the periphery of the third layer and adapted to measure a third temperature value at the periphery of the third layer, where the difference between the second and the third temperature values indicates the horizontal heat flux within the third layer.

In one embodiment, the temperature sensor further comprises a side heater arranged at the periphery of the third layer adapted to be tuned oppositely to the heat until a zero horizontal heat flux is reached in the third layer.

It is thus possible to prevent lateral heat loss, but the biggest source of lateral heat loss is heat that is escaping from the brain that is not going vertically, but diagonally. Using an additional side thermistor along with the thermistor in the third layer makes it possible to detect the lateral heat flux. It is therefore possible to operate the side heater such that the lateral heat flux becomes zero. This makes the temperature profile uniform in the lateral direction, reducing the problem to one dimension.

According to a second aspect, the present invention relates to a garment comprising said temperature sensor integrated therein such that when the garment is placed onto the body or is being worn by the body the at least one third layer becomes in contact to the skin of the surface of the body. As mentioned previously, such garment may as an example include a cap, baby cap, headband, shirt, diaper and belt, and even into a bed object such as a pillow, blanket or seat which is in contact with the body and the like.

The aspects of the present invention may each be combined with any of the other aspects. These and other aspects of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
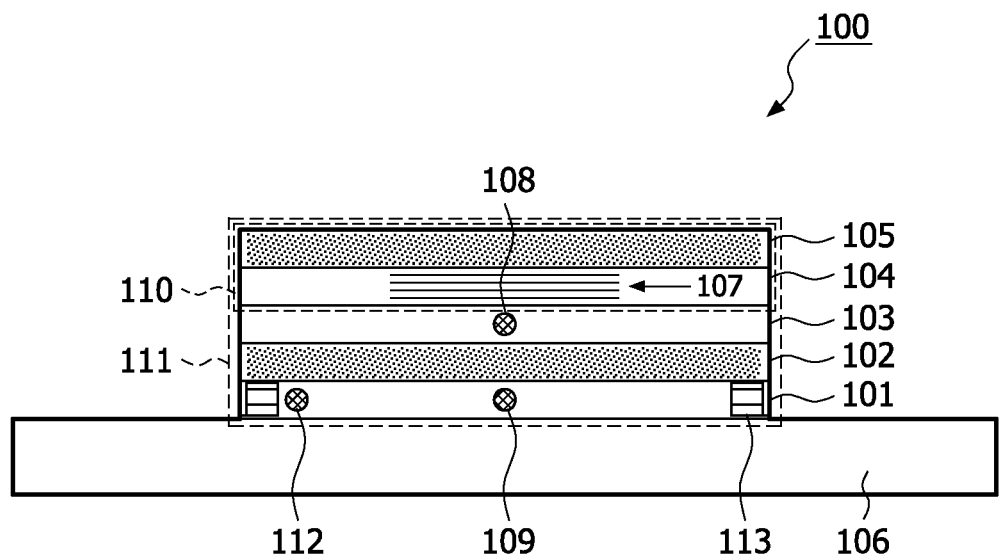
FIG. 1 shows one embodiment of a temperature sensor for body temperature measurements according to the present invention.

FIG. 1 shows one embodiment of a temperature sensor 100 for body temperature measurements according to the present invention. The temperature sensor 100 comprises a first layer 104 having a central heater 107 embedded therein, a second layer 103 attached to the first layer 104 having at least one first thermistor (Ttop) 108 embedded therein for measuring a first temperature value $t^{first}$, a third layer 101 having at least one second thermistor (Tbottom) 109 embedded therein separated from the first thermistor (Ttop) 108 for measuring at least one second temperature value $t^{second}$. The third layer 101 is adapted to be in contact to the skin of the surface 106 of the body for conducting the heat escaping from the body through the layers. The difference between the first and the second temperature values, i.e. $t^{second}-t^{first}$ indicates the vertical heat flux from the body. The central heater 107 is adapted to be tuned oppositely to the vertical heat flux $t^{second}-t^{first}$ until a zero heat flux is reached, i.e. until $t^{second}=t^{first}$. At this zero vertical heat flux, the temperature at the second thermistor (Tbottom) 109 at zero heat flux indicates the body temperature, or more particularly the core body temperature. The fabric layers may be made of woven or non-woven fabrics. The thickness of each layer is typically in the millimeter range, but may just as well be less than a millimeter.

The second layer 103 and the third layer 101 further comprise a woven, stitched or knitted conductive circuit, respectively, to which the thermistors in the respective layers are attached to. The thermistor can be attached by soldering, clamping or using conductive epoxy or Anisotropic Conductive Foil/paste (ACF/ACP). The conductive circuit may be made of a (common) ground and a signal line using e.g. conductive yarn that is stitched, woven, knitted or laminated to/into a fabric. In one embodiment, the conductive circuit is made of conductive material having a resistance lower 20 ohm/meter.

The first, second and at least the third layer are fabric layers 104, 103, 101 may be stitched or laminated together, interwoven, or combination thereof which makes the sensor soft, flexible and thin.

In one embodiment, the temperature sensor 100 further comprises a top layer 105 made of insulating material, which may be transparent, e.g. so as for illustrative purposes such as to show a nice illustrative shape (a picture).

In one embodiment, the first and second layers 104, 103 are made of the same fabric and form a part of a single layer 110 containing both the thermistor (Ttop) 108 and the heating element 107 on the same fabric, such that this single layer 110 comprises both the thermistor (Ttop) 108 and the heating element 107. A care must be taken to prevent shorts between the thermistor (Ttop) 108 and the heating element 107.

In one embodiment, the third layer 101 and the thermistor (Tbottom) 109 along with the first and second layers 104, 103 form a part of a single layer 111 on the same fabric. It is possible with 3D knitting technologies to make spacerfabrics integrated with two (or more) top layers.

In one embodiment, the second and the at least the third layers are separated by a flexible heat insulating layer 102, made of e.g. neoprene (polychloroprene), ethylene propylene diene monomer (PVDF, EPDM), and foam type materials polyethylene (PE), polypropylene (PP), methylacrylate (EMA), ethylenevinylacetate (EVA), polyolefin.

Referring to the embodiment shown in FIG. 1, the five layers 101-104 may be stitched or laminated together, or it is also possible to combine several of the layers into one fabric.

In one embodiment, the central heater 107 has a cross section that is adapted to the depth of measurement such that the larger the depth is to be measured, the larger should the cross section of the heater be. An example of a cross section is a cross section within millimeter up to few centimeters. The central heater can be made by stitching, weaving, knitting or laminating conductive yarns to/into a fabric, where the conductive yarns may be (but not necessarily) surrounded by an insulating polymer layer, or it may be printed onto the first layer using conductive ink or conductive paste. In one embodiment, the resistance of the heater is such that it can deliver around 100 mW. Referring to the setup shown in FIG. 1, this corresponds to resistances between 5 and 50 ohm. This can be achieved by matching the length of the conductive wire with the resistance. As an example, 80 Ohm/m stainless steel wire of 25 cm is 20 Ohm. The shape of the central heater should preferably be such that it gives rise to a homogeneous temperature profile in the lower layers. This shape could as an example be a spiral, but other shapes are of course also possible.

The third layer 101 is a fabric layer that incorporates at least one thermistor, and a conductive circuit to connect the thermistor. The thermistor can be attached by soldering, clamping or using conductive epoxy or ACF/ACP. The conductive circuit consists of a (common) ground and a signal line and can be made using conductive yarn that is stitched, woven, knitted or laminated to/into a fabric. The conductive circuit can be made in or as part of an illustrative design, or for hygienic layer/coating such that it becomes in contact with the skin (106).

In one embodiment, the temperature sensor 100 further comprises a transmitter (not shown) for transmitting the temperature measured at the at least one second thermistor at zero heat flux to an external monitoring device comprising a receiver. Such a monitoring device may as an example be a babyphone or some external monitoring unit that further comprises a processing unit that monitors that baby temperature continuously during the first days.

It should be noted that the temperature sensor 100 is not limited to this particular number of layers. The number of layers may just as well include more than four or five layers, also the number of thermistors does not necessarily be limited to the two thermistors 108 and 109, but three or more may just as well be implemented to measure the vertical heat flux.

Until now, the measured heat flux is a vertical heat flux which is proportional to $t^{second}-t^{first}$.

In one embodiment, the temperature sensor 100 further comprises a side thermistor (Tside) 112 arranged at the periphery of the third layer 101 and adapted to measure a third temperature value $t^{third}$ at the periphery of the third layer 101. The difference between the second and the third temperature values, i.e. $t^{third}-t^{second}$ indicates the horizontal heat flux within the third layer 101. To compensate the heat loss due to the horizontal heat flux, a side heater 113 is arranged at the periphery of the third layer adapted to be tuned oppositely to the heat flux $t^{third}-t^{second}$ until a zero horizontal heat flux is reached in the third layer. In one embodiment, the side heater 113 has substantially the same geometry as the third layer, e.g. a ring (if the third layer is a ring) made of similar elements as discussed previously in conjunction with the central heater. Accordingly, the side heater 113 is controlled by the horizontal heat flux, whereas the central heater 107 is controlled by the vertical heat flux. One of the reasons of using such a side heater 113 is to prevent lateral heat loss. The biggest source of lateral heat loss is heat that is escaping from the brain that is not going vertically, but diagonally. So the temperature profile in the skull becomes 2-dimensional. The side heater makes the temperature profile uniform in the lateral direction, reducing the problem to 1 dimension. The thermistor 112 at the periphery is used to detect this lateral temperature profile. A minor source of lateral heat loss is heat that is escaping from the center of the sensor to the side of the sensor. But this is minimal, given the flatness of the sensor.

In one embodiment, the temperature sensor 100 is integrated into patch (not shown), where the patch further comprises a system 200 (see FIG. 2) comprising a processing unit (P) 201 such as a microprocessor for converting the output from the at least one second thermistor at zero heat flux into the measured body temperature, a battery (B) 203, and an indicator means (I_M) 202 for indicating the measured body temperature. The indicator means (I_M) 202 may as an example be a display such as a color display. The indicator means (I_M) 202 may be replaced by a transmitter (T) 204 for transmitting the measured body temperature to a monitoring device comprising a receiver (e.g. a babyphone). This patch can be made so that it is either re-usable or disposable. Accordingly, this allows unobtrusive temperature monitoring, e.g. for children with fewer.

Figure 2:
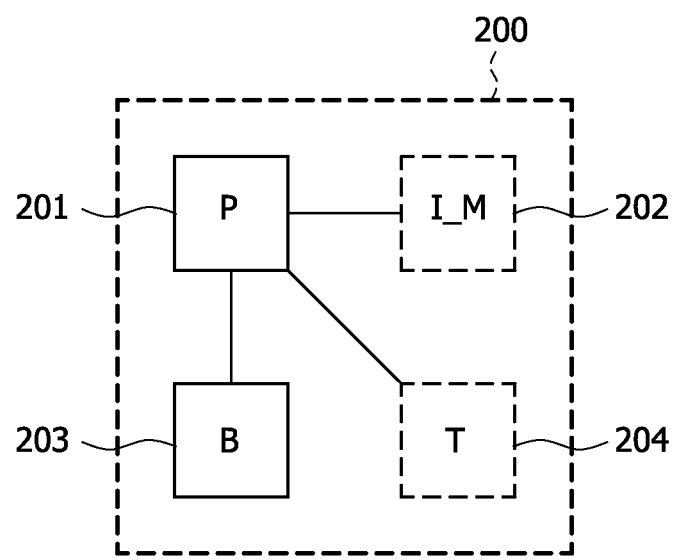
FIG. 2 shows a system adapted to be integrated into the temperature sensor or a patch or a garment.

Although not depicted here, the system 200 shown in FIG. 2 may also be integrated into the temperature sensor 100.

Figure 3:
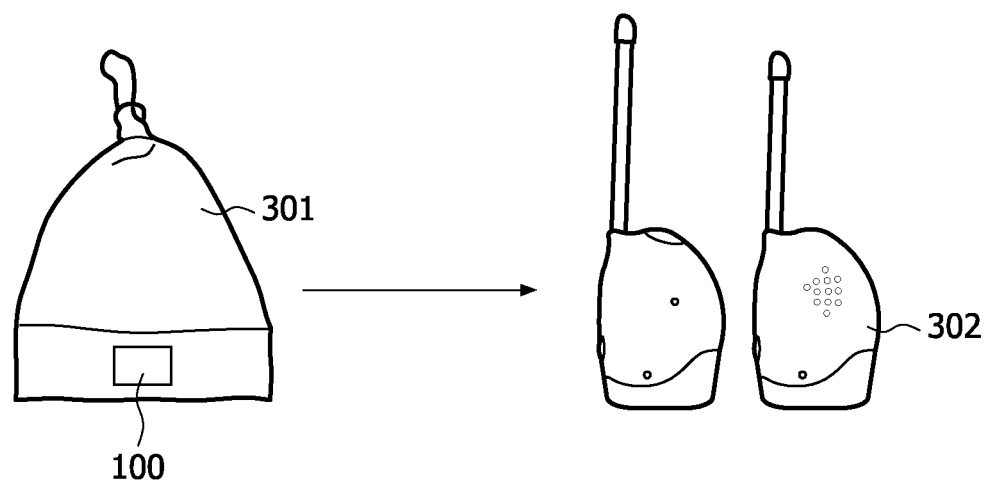
FIG. 3 shows a garment comprising the temperature sensor from FIG. 1 integrated therein.

FIG. 3 shows a garment 301 comprising the temperature sensor 100 from FIG. 1 integrated therein such that when the garment is placed onto the body or is being worn by the body the at least one third layer 101 becomes in contact to the skin of the surface 106 of the body. An example of such garment is mattress, sleeping bag, pillow, sheet, blanket, belt etc.

EXAMPLE

During the first days, newborns can have difficulties to keep a constant temperature. Therefore, it is recommended to measure the temperature frequently, and adjust clothing and heating accordingly. Too cold is not good, but overheating is even more dangerous. Present babyphones show the temperature of the room, but not of the baby.

In this example the temperature sensor 100 is integrated into a baby cap 301 such that when the baby cap is worn by the baby the sensor becomes automatically well positioned on the forehead for the measurement. This allows measuring the temperature of the baby continuously during the first days and displayed via e.g. a wireless link on the babyphone 302. However, integration possibilities are not limited to a baby cap; but could be extended to any fabric (mattress, sleeping bag, pillow, sheet, blanket, etc.) surrounding the baby. In this example, the cap 201 further comprises the system shown in FIG. 2, namely a battery (B) 203, a microcontroller (M_C) 205 for signal processing. However, instead of the indicator means (I_M) 202 the system comprises a transmitter (T) 204 to transmit the signal to the babyphone 202. For clinical applications, the signal may be sent to a wireless patient monitoring system or a bedside monitor.

Certain specific details of the disclosed embodiment are set forth for purposes of explanation rather than limitation, so as to provide a clear and thorough understanding of the present invention. However, it should be understood by those skilled in this art, that the present invention might be practiced in other embodiments that do not conform exactly to the details set forth herein, without departing significantly from the spirit and scope of this disclosure. Further, in this context, and for the purposes of brevity and clarity, detailed descriptions of well-known apparatuses, circuits and methodologies have been omitted so as to avoid unnecessary detail and possible confusion.

Reference signs are included in the claims, however the inclusion of the reference signs is only for clarity reasons and should not be construed as limiting the scope of the claims.

The invention claimed is:

1. A temperature sensor for body temperature measurements comprising:
    a first fabric layer having a central heater embedded therein;
    a second fabric layer attached to the first layer having at least one first thermistor embedded therein for measuring a first temperature value;
    at least one third fabric layer having at least one second thermistor embedded therein separated from the first thermistor for measuring at least one second temperature value, the at least one third layer being configured to contact skin of a body for conducting a heat flux escaping from the body through the layers, a difference between the first and the second temperature values indicating the heat flux from the body;
    a processing unit which (1) controls heat emitted from a central heater to tune the emitted heat oppositely to the heat flux until a zero heat flux is reached and (2) reads out the temperature at the at least one second thermistor at zero heat flux which indicates the body temperature; and
    a transmitter for transmitting the temperature measured at the at least one second thermistor at zero heat flux to an external monitoring device comprising a receiver.

2. The temperature sensor according to claim 1, wherein the first and the second layers are made of the same fabric and form a single functional layer having the heater and the first thermistor embedded therein such that the heater and the first thermistor are separated from each other.

3. The temperature sensor according to claim 1, wherein the fabric layers are made of woven or non-woven fabrics.

4. A garment including:
a baby cap; and
the temperature sensor according to claim 1, in the baby cap and positioned such that the third layer contacts the skin of a baby to monitor the body temperature of the baby.

5. The temperature sensor according to claim 1, further including:
a side thermistor arranged at the periphery of the third layer to measure a third temperature value at the periphery of the third layer.

6. A flexible temperature sensing patch configured to be affixed to skin of a patient to measure body temperature, the patch comprising:
a first flexible layer including a flexible heater;
a second flexible layer attached to the first layer and carrying a first thermistor for measuring a first temperature;
a third flexible layer including a second thermistor separated from the first thermistor for measuring a second temperature, the third flexible layer being configured to contact the skin of the patient such that heat escaping from the patient is conducted as a heat flux through the layers, a difference between the first and the second temperature indicating the heat flux from the patient such that heat from the heater is conducted oppositely to the heat flux from the patient such that when a zero heat flux is reached, the temperature at the second thermistor indicates the body temperature of the patient;
a processing unit for converting the output from the at least one second thermistor at zero heat flux into a measured body temperature value;
a battery; and
an indicator display for displaying the measured body temperature value.

7. A garment including:
a baby cap; and
the temperature sensor according to claim 6, in the baby cap and positioned such that the third layer contacts the skin of a baby to monitor the body temperature of the baby.

8. The temperature sensor according to claim 6, wherein the layers are stitched or laminated together, interwoven, or a combination thereof.

9. The temperature sensor according to claim 8, wherein the flexible heater is stitched, or embroidered, or woven, or laminated into the first layer using conductive yarn.

10. The temperature sensor according to claim 8, wherein the flexible heater is printed onto the first layer using conductive ink or conductive paste.

11. The temperature sensor according to claim 10, wherein the heater is made of a conductive material with a resistance between 5-150 ohm/meter.

12. The temperature sensor according to claim 6, wherein the second and third layers are separated by a flexible heat insulating layer.

13. A temperature sensor for body temperature measurements comprising:
a first flexible layer including a central heater;
a second flexible layer attached to the first layer having a first thermistor embedded therein for measuring a first temperature value,
a third flexible layer having a second thermistor embedded therein separated from the first thermistor for measuring a second temperature value, the third layer being configured to contact skin of the body for conducting the heat escaping from the body through the layers, such that a difference between the first and the second temperature values indicates the heat flux from the body, and when heat flux from central heater zeroes the heat flux from the body, the temperature at the second thermistor indicates the body temperature;
a side thermistor arranged at the periphery of the third layer and which measures a third temperature value at the periphery of the third layer, such that a difference between the second and the third temperature values indicates a horizontal heat flux within the third layer.

14. The temperature sensor according to claim 13, wherein the thermistors are attached to a woven, stitched or knitted conductive circuit.

15. The temperature sensor according to claim 14, wherein the conductive circuit is made of conductive material having a resistance lower 20 ohm/meter.

16. The temperature sensor according to claim 13, further comprising an insulating layer on top of the first layer.

17. The temperature sensor according to claim 13, wherein the temperature sensor is integrated into patch.

18. The temperature sensor according to claim 13, further comprising:
a side heater is arranged at the periphery of the third layer and configured to cause a heat flux opposite to the horizontal heat flux from the body.

19. A garment comprising the temperature sensor as claimed in claim 13 integrated therein such that when the garment is placed onto the body or is being worn by the body the third layer contacts the skin of the body.

* * * * *